United States Patent
Wang et al.

(10) Patent No.: US 10,125,351 B2
(45) Date of Patent: Nov. 13, 2018

(54) INDUSTRIAL PREPARATIONS OF NATURAL KILLER (NK) CELLS AND INJECTIONS CONTAINING NK CELLS

(71) Applicants: Qinyi Wang, Ningxia (CN); Huailin Wang, Ningxia (CN)

(72) Inventors: Qinyi Wang, Ningxia (CN); Huailin Wang, Ningxia (CN)

( * ) Notice: Subject to any disclaimer, the term of this patent is extended or adjusted under 35 U.S.C. 154(b) by 0 days.

(21) Appl. No.: 14/420,141

(22) PCT Filed: Dec. 19, 2012

(86) PCT No.: PCT/CN2012/086898
§ 371 (c)(1),
(2) Date: Feb. 6, 2015

(87) PCT Pub. No.: WO2014/026457
PCT Pub. Date: Feb. 20, 2014

(65) Prior Publication Data
US 2015/0218518 A1   Aug. 6, 2015

(30) Foreign Application Priority Data

Aug. 15, 2012   (CN) .......................... 2012 1 0288669

(51) Int. Cl.
*C12N 5/0783*   (2010.01)
*A61K 35/17*    (2015.01)
*A61K 35/00*    (2006.01)

(52) U.S. Cl.
CPC ............ *C12N 5/0646* (2013.01); *A61K 35/17* (2013.01); *A61K 35/00* (2013.01); *C12N 2501/23* (2013.01); *C12N 2501/2301* (2013.01); *C12N 2501/2302* (2013.01); *C12N 2501/2307* (2013.01); *C12N 2501/24* (2013.01); *C12N 2501/40* (2013.01); *C12N 2501/515* (2013.01)

(58) Field of Classification Search
None
See application file for complete search history.

(56) References Cited

U.S. PATENT DOCUMENTS

| | | | |
|---|---|---|---|
| 2003/0068306 A1* | 4/2003 | Dilber ................. | C12N 5/0646 424/93.7 |
| 2004/0162679 A1* | 8/2004 | Li ........................ | C12Q 1/6881 702/20 |

FOREIGN PATENT DOCUMENTS

| | | |
|---|---|---|
| CN | 101314761 A | 12/2008 |
| CN | 100485029 C | 5/2009 |
| CN | 102533648 A | 7/2012 |

OTHER PUBLICATIONS

MedicineNet.com (2016).*
Fortuine, R. (The Words of Medicine, Thomas, CC., Publ., 2000).*
TakaRa (2016).*
GE Healthcare Life Sciences (Application note 28-9936-25 AA, Apr. 2011, pp. 1-8, Uppsala, Sweden).*
Bonham-Carter and Shevitz (BioProcess International, Oct. 2011, 11 pages).*
Lopez-Verges et al (Blood, 2010 116(919): 3865-3874).*
Morice, W.G . (Am J Clin Pathol, 2007 127: 881-886).*
Sivori et al (Eur. J. Immunol. 2003 33: 3439-3447).*
Schmidt-Wolf et al (Brit. J. Haematol. 1994, 87: 453-458).*
MedicineNet.com (2012) (Year: 2012).*

* cited by examiner

*Primary Examiner* — G. R. Ewoldt
*Assistant Examiner* — Marianne Dibrino
(74) *Attorney, Agent, or Firm* — Klarquist Sparkman, LLP

(57) ABSTRACT

An industrial preparation of natural killer cells (NKs) is produced by: using umbilical cord blood and peripheral blood from legitimate sources as raw materials, obtaining stem cells by a method for extracting and separating karyocytes, or using FICOLL® or PERCOLL® density gradient media centrifugation to isolate and screen out karyocytes; diluting the above-mentioned karyocytes with cell culture medium, adding interferon, interleukin, CD3 antibody, and human albumin, loading them together into a bioreactor for perfusion culture, and then performing multiplication culture; the passage number of natural killer cells from multiplication culture is no less than 8, and the culture time is no less than 4 weeks; the markers of the natural killer cells obtained after the multiplication culture are $CD3^-\backslash CD56^+$, $CD16^+$, $CD57^+$, and $CD8^+$, wherein $CD16^+/CD56^+ \geq 15\%$, $CD3^-/CD56^+ \geq 50\%$, and $CD8^+/CD57^+ \geq 8\%$; then preparing an injection with a certain concentration using the cell suspension obtained by above-mentioned method.

7 Claims, No Drawings

INDUSTRIAL PREPARATIONS OF NATURAL KILLER (NK) CELLS AND INJECTIONS CONTAINING NK CELLS

TECHNICAL FIELD

This invention relates to a method for preparing natural killer (NK) cells in large-scale industrial production by using the karyocytes from human umbilical cord blood or peripheral blood as seed cells, especially to the natural killer cells and injection thereof industrially prepared by using human allogeneic karyocytes.

BACKGROUND

Natural killer cells (NK cells) are human innate immune cells, of which the major representative surface markers are $CD3^-$, $CD56^+$, $CD16^+$, $CD57^+$, and $CD8^+$. Such cells are characterized in that they contain perforin and telomerase, and can lyse the tumor cells sensitive to NK cells without prior sensitization, thereby killing the tumor cells. Natural killer cells are the major cells that mediate antibody-dependent cytotoxic effect, which express several ligands of tumor necrosis factor family and may result in apoptosis of a variety of target tumor cells. This mechanism of killing tumor cells through tumor cell apoptosis is more promising than the secretory, particles-mediated killing. Since most receptors on tumor cells are sensitive to death caused by apoptosis, natural killer cells are of great significance in terms of anti-tumor. The anti-tumor effect of natural killer cells is a fact to which the international mainstream medicine has no disputes.

Natural killer cell can cause apoptosis of various tumor cells and represents a kind of tumor immunotherapy, which has become the consensus of the international medical community. Natural killer cell is a type of human lymphocyte and is in small amounts, only accounting for 1-1.5% of the total lymphocytes. Therefore, how to obtain natural killer cells becomes the focus of the medical community.

Scientists cultured autologous peripheral blood cells from patients with cell inducing factors for 2-4 weeks and made $CD3^+$ and $CD56^+$ cells increase by 5-10%. The killer lymphocytes obtained therefrom were referred to as cytokine-induced killer (CIK) cells. Some scientists used the pre-prepared mesenchymal stem cells (MSC) to induce and cultivate natural killer cells in vitro, or used hematopoietic stem cells to induce and cultivate natural killer cells. All these methods for obtaining natural killer cells have certain limitations. For patients with advanced tumor, whether they will be treated with CIK cells depends on not only the decision of the physician, but also culture time and culture conditions. Natural killer cells require longer culture time than the disease progression in cancer patients, and thus have limited clinical application.

Natural killer lymphocytes are the medical community recognized cellular therapy for anti-tumor cell and immunity. Clinically, such cellular therapy comprises: isolating mononuclear cells from the peripheral blood from patients, adding cell inducing factors, performing culture and expansion in vitro for 2-6 weeks with the aim of allowing the mononuclear cells to develop into T lymphocytes (surface markers are $CD3^+$ and $CD56^+$), and returning the cells to the patients after they reach to a certain number. In normal human body, $CD3^+$ and $CD56^+$ cells are present in small number, while after expanded for 2-6 weeks through induced culture in vitro, $CD3^+$ and $CD56^+$ cells respectively reach at least 20% and 5%. Natural killer cell therapy gets some clinical efficacy in personalized treatment and significantly increases the five-year survival rate. However, there are still limitations in the development and promotion of clinical therapy.

Firstly, in this technique, the killer lymphocytes are cultured and expanded for clinical therapy by using mononuclear cells as carrier and adding cell inducing factors. So far, nearly all the NK cell therapies worldwide adopt one-to-one personalized treatment. That is, mononuclear cells from a patient are directly collected or indirectly collected by isolating mononuclear cells from the donor blood of a patient, and then the mononuclear cells were induced, expanded in vitro, and used to treat various solid tumors in the patient. Since this traditional therapy is a one-to-one personalized treatment method, it can only be carried out at bedside in hospital.

Secondly, in this therapy, it generally takes 2-6 weeks to prepare natural killer cells. For patients with advanced tumor, especially the patients subjected to radiotherapy and chemotherapy after surgery, some of them may pass away before the preparation of cells is completed, or the resultant cells are returned.

Thirdly, as for the one-to-one therapy, a complete processes of cell induction and expansion culture need to be conducted for each person. From the view of laboratory management, it is hard to control internal quality, not to mention the external quality. Although this is an excellent medical technology, it is difficult to promote and spread. Not all patients share equal therapeutic opportunity.

Fourthly, theoretically, CIK cells prepared as described above are induced, cultured and expanded from adult stem cells, which are contained in the culture medium in large amount and can produce CIK cells through unlimited expansion. However, clinically, after expanded for 5-6 weeks, their expansion rate decreases significantly and the expansion amount (doubling number) is obviously less than that at the early stages. Furthermore, with the expansion generation increased, their immune killing effects on tumor cells also reduce. Therefore, it is vital to control and grasp the number of subculture of natural killer cells, while maintaining the biological activity of natural killer cells is more important.

Fifthly, in the conventional methods, mononuclear cells or hematopoietic stem cells derived from patients are used as primary cells, and cytokines are used to induce CIK cells. As for these mononuclear cells from tumor patients, the mononuclear cells of some patients share common antigenicity with their tumor cells; therefore, the induced anti-tumor ability of CIK cells tends to be poor when the mononuclear cells from these patients are used as primary cells.

It has been verified by scientists that allogeneic umbilical cord blood karyocytes contain abundant stem cells, the biological activity of such stem cells is superior to that of the stem cells derived from autologous bone marrow and autologous peripheral blood. This is a population of stem cells with the potential of multiple differentiation and expansion generation. Stem cells are have many types, comprising hematopoietic stem cells (HSC), mesenchymal stem cells (MSC), unrestricted somatic stem cells (USSCs), cord blood-derived embryonic-like stem cells (CBEs), cord blood-derived multipotent adult progenitor cells (CB-MPCs).

Although the allogeneic peripheral blood karyocytes contain less abundant stem cells than umbilical cord blood, they contain hematopoietic stem cells, mesenchymal stem cells, small amounts of cord blood-derived multipotent adult progenitor cells (CB-MPCs).

There are numerous methods for extracting and separating karyocytes from umbilical cord blood and peripheral blood. The extraction methods involved in the present invention are the method in the applicant's prior granted patent "A kit for separating karyocytes in vitro and application method thereof" (Patent No. ZL200610106875.5) and the technique for using FICOLL® or PERCOLL® density gradient media (GE Healthcare Bioprocess R&D AB, Uppsala, Sweden) centrifugation to isolate and screen out karyocytes.

SUMMARY OF THE INVENTION

It is an object of the invention to overcome the disadvantages in the prior art and provide natural killer cells and injection thereof industrially prepared by using human allogeneic karyocytes.

The object of the present invention is achieved in accordance with the protocol described below:

A method for preparing natural killer cells from umbilical cord blood or peripheral blood, comprising:

using umbilical cord blood and peripheral blood as raw materials, obtaining stem cells by a method for extracting and separating karyocytes or using FICOLL® or PERCOLL® density gradient media centrifugation to isolate and screen out karyocytes;

diluting the above-mentioned karyocytes with cell culture medium, adding interferon, interleukin, CD3 antibody, and human albumin, loading them together into a bioreactor for perfusion culture, and then performing multiplication culture, wherein the passage number of natural killer cells from multiplication culture is no less than 8, and the culture time is no less than 4 weeks; the markers of the natural killer cells obtained after the multiplication culture are $CD3^-$, $CD56^+$, $CD16^+$, $CD57^+$, and $CD8^+$, wherein $CD16^+/CD56^+ \geq 15\%$, $CD3^-/CD56^+ \geq 50\%$, and $CD8^+/CD57^+ \geq 8\%$.

According to the invention, the umbilical cord blood derived from the umbilical cord blood bank or the peripheral blood derived from center blood banks is used, from which karyocytes are extracted and separated as seed cells provided that the umbilical cord blood or peripheral blood is from legitimate sources and healthy donors. The extraction technique adopts the method in the applicant's proprietary "a kit for processing bone marrow and umbilical cord blood cells" (Patent No. ZL200610106875.5) to isolate and extract umbilical cord blood stem cells; or uses FICOLL® or PERCOLL® density gradient media centrifugation to screen out karyocytes.

The above cell culture medium is serum-free medium GT-T551 or RPMI-1640 cell culture medium.

The above interferon is gamma-interferon (IFN-γ).

The above interleukin is one of interleukin-2 (IL-2), interleukin-1 (IL-1), and interleukin-7 (IL-7), or a combination thereof.

The temperature of the above perfusion culture is 37° C.

The above multiplication culture is carried out in a bioreactor or in a perfusion incubator for industrial use.

The markers of the natural killer cells obtained after the multiplication culture are $CD3^-$, $CD56^+$, $CD16^+$, $CD57^+$, and $CD8^+$, wherein $CD16^+/CD56^+ \geq 15\%$, $CD3^-/CD56^+ \geq 50\%$, and $CD8^+/CD57^+ \geq 8\%$.

The finished natural killer cells after multiplication culture need to be subjected to quality control test. The test items include: ① cellular CD phenotype ($CD3^-$, $CD56^+$, $CD16^+$, $CD57^+$, $CD8^+$); ② cellular chromosomal karyotype, or microarray sequencing assay; ③ sterility test; ④ endotoxin test for cell suspension≤2 EU/ml; and ⑤ cell survival rate test≥96%.

The present invention provides an injection of natural killer cell prepared industrially using human allogeneic karyocytes, which is produced as follows:

using umbilical cord blood or peripheral blood as raw materials, obtaining stem cells by a method for extracting and separating karyocytes or using FICOLL® or PERCOLL® density gradient media centrifugation to isolate and screen out karyocytes;

diluting the above-mentioned karyocytes with cell culture medium, adding interferon, interleukin, CD3 antibody, and human albumin, loading them together into a bioreactor for perfusion culture, and then performing multiplication culture, wherein the passage number of natural killer cells from multiplication culture is no less than 8, and the culture time is no less than 4 weeks; the markers of the natural killer cells obtained after the multiplication culture are $CD3^-$, $CD56^+$, $CD16^+$, $CD57^+$, and $CD8^+$, wherein $CD16^+/CD56^+ \geq 15\%$, $CD3^-/CD56^+ \geq 50\%$, and $CD8^+/CD57^+ \geq 8\%$; and preparing an injection with a certain concentration using the cell suspension obtained by above-mentioned method, thus obtaining the finished product.

The above cell culture medium is serum-free medium GT-T551 or RPMI-1640 cell culture medium;

The above interferon is gamma-interferon (IFN-γ);

The above interleukin is one of interleukin-2 (IL-2), interleukin-1 (IL-1), and interleukin-7 (IL-7), or a combination thereof;

The temperature of the above perfusion culture is 37° C.;

The above human albumin is pharmaceutical-grade human albumin;

The above multiplication culture is carried out in a bioreactor or in a perfusion incubator for industrial use, such as Wave by U.S. GE Corporation, or domestic industrial reaction kettle for perfusion culture.

The markers of the natural killer cells obtained after the multiplication culture are $CD3^-$, $CD56^+$, $CD16^+$, $CD57^+$, and $CD8^+$, wherein $CD16^+/CD56^+ \geq 15\%$, $CD3^-/CD56^+ \geq 50\%$, and $CD8^+/CD57^+ \geq 8\%$.

The finished natural killer cells after multiplication culture need to be subjected to quality control test. The test items include: ① cellular CD phenotype ($CD3^-$, $CD56^+$, $CD16^+$, $CD57^+$, $CD8^+$); ② cellular chromosomal karyotype, or microarray sequencing assay; ③ sterility test. ④ endotoxin test for cell suspension≤2 EU/ml; and ⑤ cell survival rate test≥96%.

After passing the test, the cell suspension is formulated into a concentration of $1 \times 10^6$ /ml, and then sub-assembled as qualified "injections of natural killer cell" for delivery, wherein the subpackage amount depends on the requirements of a clinician, with a minimum of 10 ml each for clinical use.

The finished injections of natural killer cell require refrigerated transportation and preservation (cold-chain), with an optimal preservation and transportation temperature of 4° C.

The core of the present invention lies in that karyocytes derived from allogeneic umbilical cord blood or peripheral blood are selected, induced by cell inducing factors, industrially expanded and cultured, and then formulated into injections of natural killer cell (pharmaceutical grade) for direct application by the clinician in anti-tumor therapy. Such injections are proved to be remarkably effective in clinical treatment of malignancies, such as liver cancer, uterine cancer and gastric cancer.

1. Treatment of liver cancer: suitable for the patients suspected of liver cancer metastasis after surgical removal of liver cancer, who has alpha-fetoprotein (AFP)>400 ng/ml (ELISA assay), the total number of leukocytes<$3.6 \times 10^9$/L, and other significantly decreased immune indexes. A 50 ml injection of natural killer cell with cell concentration of $1\times10^6$/ml was intravenously injected once every other day, with a total of five times for a course of treatment.

After a course of treatment was completed, the AFP level in 46% patients started to decrease at the first weekend, and the AFP level in 91.5% patients may be less than 100 ng/ml or close to normal level at the fourth weekend. Leukocyte level began to increase at the first weekend, and raised to normal level in 91% patients over two weeks (male: $3.97\sim9.15\times10^9$/L, female: $3.69\sim9.16\times10^9$/L). The general conditions of these patients improved expressly. The second and third courses of treatment were carried out at an interval of 3-6 months based on the specific states of the patients, and the two-year survival rate significantly increased by nearly 50%.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

2. Treatment of uterine cancer: suitable for the patients suspected of metastasis after surgical removal of uterine cancer, who has clinical carcinoembryonic antigen (CEA) >20 ng/ml (ELISA assay) and the significantly lower total number of leukocytes than normal level. A 50 ml injection of natural killer cell with cell concentration of $1\times10^6$/ml was intravenously injected once every other day, with a total of five times for a course of treatment.

Seven days after the uterine cancer patients were intravenously injected with the injections of natural killer cell, the CEA level in 41% patients started to decrease, and the CEA level in 95% patients was below 10 ng/ml or close to normal level of 3 ng/ml at the fourth weekend. Leukocyte level began to increase at the first weekend, and raised to normal level in 90% patients over two weeks (male: $3.97\sim9.15\times10^9$/L, female: $3.69\sim9.16\times10^9$/L). The general conditions of these patients improved expressly. The second and third courses of treatment were carried out at an interval of 3-6 months based on the specific states of the patients.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

3. Treatment of gastric cancer: suitable for the patients having metastasis after surgical removal of gastric cancer, who has clinical carcinoembryonic antigen (CEA)>20 ng/ml (ELISA assay) and the significantly lower total number of leukocytes than normal level. A 50 ml injection of natural killer cell with cell concentration of $1\times10^6$/ml was intravenously injected once every other day, with a total of three times for a course of treatment.

Seven days after the gastric cancer patients were intravenously injected with the injection of natural killer cell, the CEA level in 52% patients started to decrease, and the CEA level in 90% patients was below 10 ng/ml or close to normal level of 3 ng/ml at the fourth weekend. Leukocyte level began to increase at the first weekend, and raised to normal level in 89% patients over two weeks (male: $3.97\sim9.15\times10^9$/L, female: $3.69\sim9.16\times10^9$/L). The general conditions of these patients improved expressly. The second and third courses of treatment were carried out at an interval of 3-6 months based on the specific states of the patients.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

The present invention solves the problem as to the conventional time-consuming process for preparing natural killer cells or CIK cells in clinical, and allows the clinician to conveniently use the injection of natural killer cell (pharmaceutical grade) anytime and anywhere, so as to treat the tumor patients as early as possible. In the meantime, the present invention enables industrial production of natural killer cells such that natural killer cell therapy technology develops from a clinical technology into the medicine in form of natural killer cells injections, realizing medicalization of the cells. Thus, the present invention sets a precedent for the industrial production of cell medicine, helps our country gain a place in the field of cell therapy for developing cell medicine with intellectual property, and make the "cell medicine" with intellectual property penetrate the international market.

There are several advantages in inducing natural killer cells with inducing factors in vitro based on karyocytes derived from allogeneic umbilical cord blood and allogeneic peripheral blood, which are as follows:

1. The allogeneic umbilical cord blood is obtained from the umbilical cord blood bank, which guarantees healthy donors. The umbilical cord blood is very rich in karyocytes, and the karyocytes derived from this source meet biological security requirements.

Also, the allogeneic peripheral blood is obtained from the center blood banks around the country, which guarantees healthy donors and quality, meeting biological security requirements.

2. The method of the present invention induces natural killer cells with inducing factors based on karyocytes derived from the allogeneic umbilical cord blood and allogeneic peripheral blood, and thus enables industrial production of "injections of natural killer cells" and normalized production of cell medicine according to the standard requirements of GMP, CE or FDA.

3. The industrially produced "injections of natural killer cells" allow the convenient use by the clinician, and thus the clinician could conveniently use them to treat various cancers, as done in medicine treatment.

4. The surface markers of the induced killer lymphocytes CIK are $CD3^+$, $CD56^+$ and partly $CD16^+$, and thus they are only effective on certain cancers in the clinical anti-tumor therapy. Natural killer cells are human innate immune cells, of which the major representative surface markers are $CD3^+$, $CD56^+$, $CD16^+$, $CD57^+$, and $CD8^+$. The anti-tumor characteristics of NK cells are that they may result in apoptosis of a variety of target tumor cells, i.e. killing tumor cells by way of tumor cell apoptosis. Therefore, the method of the present invention is not only directed at $CD3^+$ and $CD56^+$ positive tumors, but also $CD16^+$, $CD57^+$ and $CD8^+$ positive tumors, having killing effects on most malignant tumors.

DETAILED DESCRIPTION OF THE INVENTION

Example 1

An umbilical cord blood sample (no less than 50 ml) from healthy donors was obtained from the umbilical cord blood bank, together with the traceable donor code, wherein the donors have neither genetic diseases nor the four infectious diseases including hepatitis B, hepatitis C, HIV/AIDS, and syphilis). For the sake of security, an additional umbilical cord blood sample of 1 ml was obtained and delivered to a third part for detecting hepatitis B, hepatitis C, HIV/AIDS, and syphilis, as well as ABO blood group and RH blood group, for archiving and future traceability.

After identified as qualified, the donor umbilical cord blood was immediately used for the preparation of karyocytes. The separation and extraction of karyocytes from the umbilical cord blood were conducted using the Bone Marrow and Umbilical Cord Blood Cells Processing Kit (Ningxia Zhonglianda Biotech Co., Ltd) according to the manufacturer's instructions.

During the separation, all the umbilical cord blood serum should be preserved and filtered through a 0.22 µm filter for further use.

The culture medium for natural killer cells is prepared as follows:

Adding the umbilical cord blood serum preserved during the preparation of the karyocytes to serum-free medium GT-T551 in a ratio of 1:200 by weight, with a total volume of about 10000 ml.

Additionally adding 0.1-0.5% (wt) human albumin (pharmaceutical grade), 20 U-200 U/ml (international unit) interleukin-2, 5-50 mg/ml CD3 monoclonal antibody, and 10 U-100 U/ml IFN-γ; and Assaying the survival rate of the isolated and extracted umbilical cord blood karyocytes, performing cell counting to obtain the total number, and then adding the culture medium for natural killer cells in a concentration of $1\times10^6$/ml calculated based on cell number, wherein the total volume of the natural killer cells culture medium is about 100-150 ml, since typically $1\times10^8$ karyocytes may be isolated and extracted from an umbilical cord blood sample, and 50 µl sample was taken and assayed for DNA using microarray sequencing, and the assay result was compared with the assay result for DNA of the finished injections of natural killer cell.

The induced natural killer cells culture medium containing the umbilical cord blood karyocytes was loaded into the Wave bioreactor (U.S. GE Corporation) for perfusion culture.

Conditions: 37° C.±0.2° C. and 5% $CO_2$.

The culture medium is mixed well by built-in agitator, with a rotating speed of 8-12 times/min.

No formulated natural killer cells culture medium was added in the first two days. From the third day, based on the cell growth speed and the calculated concentration of 1-5×$10^6$/ml, a corresponding amount of natural killer cells culture medium was added, and the perfusate was removed in a ratio of 1/2 of the added cell medium until all the formulated natural killer cells culture medium ran out. The culture was maintained for 1-2 days until the cell concentration reached $1\times10^7$/ml.

Continuous culture was conducted for 4-6 weeks, and the culture was completed when the cell density reached or was close to $1\times10^7$/ml, and the calculated total number of cells reached $1\times10^{10}$. Alternatively, continuous culture was conducted 6 weeks before the culture was completed. All the cells were collected carefully, and washed twice with cell maintenance medium.

[Assay]

Assay steps should be performed first.

A cell suspension of $1\times10^6$/ml was prepared after the processes for culturing the natural killer cells and the finished products were testified as qualified.

The cell suspension was sub-assembled into bags with a specification of $2\times10^7$/20 ml or $5\times10^7$/50 ml, and then 5% $CO_2$ was added for sealing, thereby obtaining the injections of natural killer cell (cell medicine). These injections could be directly used by the clinician for treatment, of which the preservation and transportation must be conducted at a lower temperature (an optimum temperature of 4° C.).

1. Assay of the Cell Culture Procedure (Process Quality Control)

The removed perfusate was assayed daily for bacterial endotoxin from the third day during the culture of natural killer cells (bacterial endotoxin≤5 EU/ml).

Three days before the end of the culture of natural killer cells, samples were collected daily for sterility test. The assay method used herein is described in the supplementary provisions of *Chinese Pharmacopoeia* 2010.

A cell morphology test must be performed weekly during the culture of natural killer cells, for observing the karyotype and cell size, and determining whether the cell morphology is normal.

2. The Assay of the Finished Injection of Natural Killer Cell

After the culture of the natural killer cells was completed, upon the concentration and washing of cells, the culture medium was sampled and assayed (bacterial endotoxin≤5 EU/ml).

The culture medium was sampled and assayed for *mycoplasma*, and the result should be negative. The assay method used herein is described in Part 6, Chapter 5 of *National Guide to Clinical Laboratory Procedures*, Third Edition, edited by Department of Medical Administration, Ministry of Health.

The flow cytometry was used to assay the cell phenotype antigen of the natural killer cells injections. The test items and normal values were as follows: $CD3^-$, $CD56^+$, $CD16^+$, $CD57^+$, and $CD8^+$, wherein $CD16^+/CD56^+ \geq 15\%$, $CD3^-/CD56^+ \geq 50\%$, and $CD8^+/CD57^+ \geq 8\%$.

The cell survival rate was assayed by using trypan blue staining method, wherein the product with the assay result of survival rate≥96% was qualified, otherwise unqualified.

50 µl of the product was assayed for DNA using microarray sequencing. The assay result was compared with the DNA of primary cells to determine if there was any variation: no DNA variation indicates that the product is normal and qualified. The assay results of this Example are shown in Table 1.

TABLE 1

The assay results of NK cells

| No. | test items | qualified criteria that are designed | found | results |
|---|---|---|---|---|
| 1 | bacterial endotoxin | ≤5 EU/ml | ≤5 EU/ml | qualified |
| 2 | mycoplasma | negative | negative | qualified |
| 3 | $CD16^+/CD56^+$ | ≥15% | 18% | qualified |
| 4 | $CD3^-/CD56^+$ | ≥50% | 80% | qualified |
| 5 | $CD8^+/CD57^+$ | 8% | 8.5% | qualified |
| 6 | cell survival rate | ≥96% | 98% | qualified |
| 7 | DNA assay | no variation | no variation | qualified |

After the above items all pass the test, this batch of natural killer cell injections are confirmed as qualified medicines, and can be sub-assembled and labeled for delivery. The natural killer cell injections of each batch are required to be traceable, and the samples should be cryopreserved for more than five years.

The above natural killer cells injections were used to treat the patients suspected of liver cancer metastasis after surgical removal of liver cancer, who has alpha-fetoprotein (AFP)>400 ng/ml (ELISA assay), the total number of leukocytes<$3.6 \times 10^9$/L, and other significantly decreased immune indexes. A 50 ml injection of natural killer cell with cell concentration of $1 \times 10^6$/ml was intravenously injected once every other day, with a total of five times for a course of treatment.

After a course of treatment was completed, the AFP level in 46% patients started to decrease at the first weekend, and the AFP level in 91.5% patients may be less than 100 ng/ml or close to normal level at the fourth weekend. Leukocyte level began to increase at the first weekend, and raised to normal level in 91% patients over two weeks (male: $3.97 \sim 9.15 \times 10^9$/L, female: $3.69 \sim 9.16 \times 10^9$/L). The general conditions of these patients improved expressly. The second and third courses of treatment were carried out at an interval of 3-6 months based on the specific states of the patients, and the two-year survival rate significantly increased by nearly 50%.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

Example 2

A 200 ml peripheral blood sample from healthy donors was obtained from center blood banks, wherein the sample has the assay report about four infectious diseases including hepatitis B, hepatitis C, HIV/AIDS and syphilis, together with the traceable donor code. For the sake of security, an additional blood sample of 1 ml was obtained and delivered to a third part for detecting hepatitis B, hepatitis C, HIV/AIDS, and syphilis, as well as ABO blood group and RH blood group, for archiving and future traceability.

After identified as qualified, the donor peripheral blood was immediately used for the preparation of karyocytes. The separation and extraction of karyocytes from the peripheral blood were conducted using the Bone Marrow and Umbilical Cord Blood Cells Processing Kit (Ningxia Zhonglianda Biotech Co., Ltd) according to the manufacturer's instructions.

During the separation, all the peripheral blood serum should be preserved and filtered through a 0.22 μm filter for further use.

The culture medium for natural killer cells is prepared as follows:

Adding the peripheral blood serum preserved during the preparation of the karyocytes to serum-free medium GT-T551 in a ratio of 1:100 by weight, with a total volume of about 10000 ml.

Additional adding the following components:
0.1% (wt) human albumin (pharmaceutical grade);
20 U/ml (international unit) interleukin-1;
5 mg/ml CD3 monoclonal antibody; and
10 U/ml IFN-γ.

Assaying the survival rate of the isolated and extracted peripheral blood karyocytes, performing cell counting to obtain the total number, and then adding the culture medium for natural killer cells in a concentration of $1 \times 10^6$/ml calculated based on cell number, wherein the total volume of the natural killer cells culture medium is about 200 ml, since typically $2 \times 10^8$ karyocytes may be isolated and extracted from a conventional peripheral blood sample of 200 ml.

The induced natural killer cells culture medium containing the peripheral blood karyocyte was loaded into the domestic industrial reaction kettle for perfusion culture. 50 μl sample was taken and assayed for DNA using microarray sequencing, and the assay result was compared with the assay result for DNA of the finished injection of natural killer cell.

Conditions: 37° C.±0.2° C. and 5% $CO_2$.

The culture medium is mixed well by built-in agitator, with a rotating speed of 8 times/min.

No formulated natural killer cells culture medium was added in the first two days. From the third day, based on the cell growth speed and the calculated concentration of $1-5 \times 10^6$/ml, a corresponding amount of natural killer cells culture medium was added, and the perfusate was removed in a ratio of 1/2 of the cell medium added until all the formulated natural killer cells culture medium ran out. The culture was maintained for 1-2 days until the cell concentration reached $1 \times 10^7$/ml.

Continuous culture was conducted for 4-6 weeks, and the culture was completed when the cell density reached or was close to $1 \times 10^7$/ml, and the calculated total number of cells reached $1 \times 10^{10}$. Alternatively, continuous culture was conducted 6 weeks before the culture was completed. All the cells were collected carefully, and washed twice with cell maintenance medium. The assay results of this Example are shown in Table 2.

TABLE 2

The assay results of NK cells

| No. | test items | qualified criteria that are designed | found | results |
|---|---|---|---|---|
| 1 | bacterial endotoxin | ≤5 EU/ml | ≤5 EU/ml | qualified |
| 2 | mycoplasma | negative | negative | qualified |
| 3 | CD16+/CD56+ | ≥15% | 17% | qualified |
| 4 | CD3−/CD56+ | ≥50% | 79% | qualified |
| 5 | CD8+/CD57+ | 8% | 8.3% | qualified |
| 6 | cell survival rate | ≥96% | 97% | qualified |
| 7 | DNA assay | no variation | no variation | qualified |

A cell suspension of $1 \times 10^6$/ml was prepared after the processes for culturing the natural killer cells and the finished products were testified as qualified.

The cell suspension was sub-assembled into bags with a specification of $2 \times 10^7$/20 ml or $5 \times 10^7$/50 ml, and then 5% $CO_2$ was added for sealing, thereby obtaining the injections of natural killer cell (cell medicine). These injections could be directly used by the clinician for treatment, of which the preservation and transportation must be conducted at a lower temperature (an optimum temperature of 4° C.).

[Assay]

The assays of cell culture procedure and the finished injection of natural killer cell are the same as those in Example 1.

The finished injection of natural killer cell was used to treat the patients suspected of metastasis after surgical removal of uterine cancer, who has clinical carcinoembryonic antigen (CEA)>20 ng/ml (ELISA assay) and the significantly lower total number of leukocytes than normal level. A 50 ml injection of natural killer cell with cell concentration of 1×10⁶/ml was intravenously injected once every other day, with a total of five times for a course of treatment.

Seven days after the uterine cancer patients were intravenously injected with the injections of natural killer cell, the CEA level in 41% patients started to decrease, and the CEA level in 95% patients was below 10 ng/ml or close to normal level of 3 ng/ml at the fourth weekend. Leukocyte level began to increase at the first weekend, and raised to normal level in 90% patients over two weeks (male: $3.97~9.15\times10^9$/L, female: $3.69~9.16\times10^9$/L). The general conditions of these patients improved expressly. The second and third courses of treatment were carried out at an interval of 3-6 months based on the specific states of the patients.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

Example 3

An umbilical cord blood sample (no less than 50 ml) from healthy donors was obtained from the umbilical cord blood bank, together with the traceable donor code, wherein the donors have neither genetic diseases nor the four infectious diseases including hepatitis B, hepatitis C, HIV/AIDS, and syphilis). For the sake of security, an additional umbilical cord blood sample of 1 ml was obtained and delivered to a third part for detecting hepatitis B, hepatitis C, HIV/AIDS, and syphilis, as well as ABO blood group and RH blood group, for archiving and future traceability.

After identified as qualified, the donor umbilical cord blood was immediately used for the preparation of karyocytes. FICOLL® or PERCOLL® density gradient media centrifugation was used to sort out mononuclear cells.

1. The whole blood of umbilical cord blood was added into a 50 ml centrifuge tube, and centrifuged at 800×g for 5 minutes. All the umbilical cord blood serum was collected carefully, and filtered and sterilized through a 0.22 μm filter for further use.

2. The red blood cells and white blood cells deposited at the bottom of the centrifuge tube were dissolved with PBS solution, and the total volume was identical with that of this umbilical cord blood.

3. Monocytes (karyocytes) were sorted out from the dissolved red blood cells and white blood cells using FICOLL® or PERCOLL® density gradient media centrifugation, and calculated for the total cell number.

The culture medium for natural killer cells is prepared as follows:

Adding the umbilical cord blood serum preserved during the preparation of the karyocytes to serum-free medium RMP I-1640 in a ratio of 1:200, with a total volume of around 10000 ml.

Additionally adding 0.5% (wt) human albumin (pharmaceutical grade), 200 U/ml (international unit) interleukin-7, 50 mg/ml CD3 monoclonal antibody, and 100 U/ml IFN-γ.

Assaying the survival rate of the isolated and extracted umbilical cord blood karyocytes, performing cell counting to obtain the total number, and then adding the culture medium for natural killer cells in a concentration of 1×10⁶/ml calculated based on cell number, wherein the total volume of the natural killer cells culture medium is about 100-150 ml, since typically 1×10⁸ karyocytes may be isolated and extracted from an umbilical cord blood sample, and 50 μl sample was taken and assayed for DNA using microarray sequencing, and the assay result was compared with the assay result for DNA of the finished injections of natural killer cell.

The induced natural killer cells culture medium containing the umbilical cord blood karyocytes was loaded into the Wave bioreactor (U.S. GE Corporation) for perfusion culture.

Conditions: 37° C.±0.2° C. and 5% $CO_2$.

The culture medium is mixed well by built-in agitator, with a rotating speed of 8-12 times/min.

No formulated natural killer cells culture medium was added in the first two days. From the third day, based on the cell growth speed and the calculated concentration of 1-5×10⁶/ml, a corresponding amount of natural killer cells culture medium was added, and the perfusate was removed in a ratio of 1/2 of the cell medium added until all the formulated natural killer cells culture medium ran out. The culture was maintained for 1-2 days until the cell concentration reached 1×10⁷/ml.

Continuous culture was conducted for 4-6 weeks, and the culture was completed when the cell density reached or was close to 1×10⁷/ml, and the calculated total number of cells reached 1×10¹⁰. Alternatively, continuous culture was conducted 6 weeks before the culture was completed. All the cells were collected carefully, and washed twice with cell maintenance medium. The assay results of this Example are shown in Table 3.

TABLE 3

The assay results of NK cells

| No. | test items | qualified criteria that are designed | found | results |
|---|---|---|---|---|
| 1 | bacterial endotoxin | ≤5 EU/ml | ≤5 EU/ml | qualified |
| 2 | mycoplasma | negative | negative | qualified |
| 3 | CD16⁺/CD56⁺ | ≥15% | 17% | qualified |
| 4 | CD3⁻/CD56⁺ | ≥50% | 81% | qualified |
| 5 | CD8⁺/CD57⁺ | 8% | 8.2% | qualified |
| 6 | cell survival rate | ≥96% | 99% | qualified |
| 7 | DNA assay | no variation | no variation | qualified |

A cell suspension of 1×10⁶/ml was prepared after the processes for culturing the natural killer cells and the finished products were testified as qualified.

The cell suspension was sub-assembled into bags with a specification of 2×10⁷/20 ml or 5×10⁷/50 ml, and then 5% $CO_2$ was added for sealing, thereby obtaining the injections of natural killer cell (cell medicine). These injections could be directly used by the clinician for treatment, of which the preservation and transportation must be conducted at a lower temperature (an optimum temperature of 4° C.).

[Assay]

The assays of cell culture procedure and the finished injection of natural killer cell are the same as those in Example 1.

The finished injection of natural killer cell was used to treat the patients having metastasis after surgical removal of gastric cancer, who has clinical carcinoembryonic antigen (CEA)>20 ng/ml (ELISA assay) and the significantly lower total number of leukocytes than normal level. A 50 ml injection of natural killer cell with cell concentration of 1×10⁶/ml was intravenously injected once every other day, with a total of three times for a course of treatment.

Seven days after the gastric cancer patients were intravenously injected with the injection of natural killer cell, the CEA level in 52% patients started to decrease, and the CEA level in 90% patients was below 10 ng/ml or close to normal level of 3 ng/ml at the fourth weekend. Leukocyte level began to increase at the first weekend, and raised to normal level in 89% patients over two weeks (male: 3.97~9.15×$10^9$/L, female: 3.69~9.16×$10^9$/L). The general conditions of these patients improved expressly. The second and third courses of treatment were carried out at an interval of 3-6 months based on the specific states of the patients.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

Example 4

A 200 ml peripheral blood sample from healthy donors was obtained from center blood banks, wherein the sample has the assay report about four infectious diseases including hepatitis B, hepatitis C, HIV/AIDS and syphilis, together with the traceable donor code. For the sake of security, an additional blood sample of 1 ml was obtained and delivered to a third part for detecting hepatitis B, hepatitis C, HIV/AIDS, and syphilis, as well as ABO blood group and RH blood group, for archiving and future traceability.

After identified as qualified, the donor peripheral blood was immediately used for the preparation of karyocytes. The separation and extraction of karyocytes from the peripheral blood were conducted using the Bone Marrow and Umbilical Cord Blood Cells Processing Kit (Ningxia Zhonglianda Biotech Co., Ltd) according to the manufacturer's instructions.

1. The whole blood of peripheral blood was added into a 50 ml centrifuge tube, and centrifuged at 800×g for 5 minutes. All the peripheral blood serum was collected carefully, and filtered through a 0.22 μm filter for further use.

2. The red blood cells and white blood cells deposited at the bottom of the centrifuge tube were dissolved with PBS solution, and the total volume was identical with that of this peripheral blood, i.e. 200 ml.

3. Monocytes (karyocytes) were sorted out from the dissolved red blood cells and white blood cells using FICOLL® or PERCOLL® density gradient media centrifugation, and calculated for the total cell number.

The culture medium for natural killer cells is prepared as follows:

Adding the peripheral blood serum preserved during the preparation of the karyocytes to serum-free medium RMPI-1640 in a ratio of 1:100, with a total volume of around 10000 ml.

Additionally adding 0.5% (wt) human albumin (pharmaceutical grade), 100 U/ml (international unit) interleukin-7, 20 mg/ml CD3 monoclonal antibody, and 100 U/ml IFN-γ.

Assaying the survival rate of the isolated and extracted peripheral blood karyocytes, performing cell counting to obtain the total number, and then adding the culture medium for natural killer cells in a concentration of 1×$10^6$/ml calculated based on cell number, wherein the total volume of the natural killer cells culture medium is about 200 ml, since typically 2×$10^8$ karyocytes may be isolated and extracted from a conventional peripheral blood sample of 200 ml.

The induced natural killer cells culture medium containing the peripheral blood karyocyte was loaded into the bioreactor for perfusion culture.

Conditions: 37° C.±0.2° C. and 5% $CO_2$.

The culture medium is mixed well by built-in agitator, with a rotating speed of 8-12 times/min.

No formulated natural killer cells culture medium was added in the first two days. From the third day, based on the cell growth speed and the calculated concentration of 1-5×$10^6$/ml, a corresponding amount of natural killer cells culture medium was, and the perfusate was removed in a ratio of 1/2 of the cell medium added until all the formulated natural killer cells culture medium ran out. The culture was maintained for 1-2 days until the cell concentration reached 1×$10^7$/ml.

Continuous culture was conducted for 4-6 weeks, and the culture was completed when the cell density reached or was close to 1×$10^7$/ml, and the calculated total number of cells reached 1×$10^{10}$. Alternatively, continuous culture was conducted 6 weeks before the culture was completed. All the cells were collected carefully, and washed twice with cell maintenance medium.

A cell suspension of 1×$10^6$/ml was prepared after the processes for culturing the natural killer cells and the finished products were testified as qualified.

The cell suspension was sub-assembled into bags with a specification of 2×$10^7$/20 ml or 5×$10^7$/50 ml, and then 5% $CO_2$ was added for sealing, thereby obtaining the injections of natural killer cell (cell medicine). These injections could be directly used by the clinician for treatment, of which the preservation and transportation must be conducted at a lower temperature (an optimum temperature of 4° C.).

[Assay]

The assays of cell culture procedure and the finished injection of natural killer cell are the same as those in Example 1.

The finished injection of natural killer cell was used to treat the patients having metastasis after surgical removal of gastric cancer, who has clinical carcinoembryonic antigen (CEA)>20 ng/ml (ELISA assay) and the significantly lower total number of leukocytes than normal level. A 50 ml injection of natural killer cell with cell concentration of 1×$10^6$/ml was intravenously injected once every other day, with a total of three times for a course of treatment.

Seven days after the gastric cancer patients were intravenously injected with the injection of natural killer cell, the CEA level in 52% patients started to decrease, and the CEA level in 90% patients was below 10 ng/ml or close to normal level of 3 ng/ml at the fourth weekend. Leukocyte level began to increase at the first weekend, and raised to normal level in 89% patients over two weeks (male: 3.97~9.15×$10^9$/L, female: 3.69~9.16×$10^9$/L). The general conditions of these patients improved expressly. The second and third courses of treatment were carried out at an interval of 3-6 months based on the specific states of the patients.

Adverse reactions: after the intravenous injection of natural killer cell injections, low-grade fever occurs occasionally but the temperature rarely exceeds 37.6° C. Under such circumstances, physical cooling can be performed. The low-grade fever remains for one day before the patient spontaneously recovers. Occasional nausea and vomiting may also happen.

The present invention solves the problem as to the conventional time-consuming process for preparing natural killer cells or CIK cells in clinical, and allows the clinician to conveniently use the injection of natural killer cell (pharmaceutical grade) anytime and anywhere, so as to treat the tumor patients as early as possible. In the meantime, the present invention enables industrial production of natural killer cells such that natural killer cell therapy technology develops from a clinical technology into the medicine in form of natural killer cells injections, realizing medicalization of the cells. Thus, the present invention sets a precedent for the industrial production of cell medicine, helps our country gain a place in the field of cell therapy for developing cell medicine with intellectual property, and make the "cell medicine" with intellectual property penetrate the international market.

The invention claimed is:

1. A method for industrially preparing a population of natural killer (NK) cells from umbilical cord blood and/or peripheral blood, the method comprising:
   obtaining human allogeneic karyocytes comprising stem cells from umbilical cord blood and/or peripheral blood by isolating the human allogeneic karyocytes using density gradient media centrifugation;
   diluting the human allogeneic karyocytes in cell culture medium, wherein the cell culture medium is RPMI 1640;
   adding gamma interferon (IFNγ), interleukin (IL)-7, an anti-CD3 antibody, and human albumin, to the cell culture medium,
   loading the cell culture medium comprising the human allogeneic karyocytes, IFNγ, the interleukin, the anti-CD3 antibody, and the human albumin into a bioreactor or perfusion incubator for multiplication culture; and
   performing multiplication culture in the cell culture medium comprising IFNγ, the interleukin, the anti-CD3 antibody, and human albumin to culture NK cells from the human allogeneic karyocytes, wherein the time of the multiplication culture is no less than 4 weeks;
   thereby producing the population of NK cells, wherein at least 15% of the NK cells in the population are $CD16^+/CD56^+$, at least 50% of the NK cells in the population are $CD3^-/CD56^+$, and at least 8% of the NK cells in the population are $CD8^+/CD57^+$.

2. The method according to claim 1, wherein the cell culture medium is serum-free RPMI 1640.

3. The method according to claim 1, wherein the temperature for multiplication culture is 37° C.

4. The method according to claim 1, wherein the multiplication culture is carried out in the bioreactor.

5. The method according to claim 1, wherein human cord blood serum and/or human peripheral blood serum is also included in the cell culture medium loaded into the bioreactor.

6. The method according to claim 1, further comprising preparing a composition comprising a cell suspension of the NK cells from the multiplication culture.

7. The method according to claim 1, wherein no cell culture medium is added again for two days after loading the cell culture medium including the human allogeneic karyocytes, the IFNγ, the IL-7, the anti-CD3 antibody, and the human albumin into the bioreactor or the perfusion incubator.

* * * * *